(12) United States Patent
Aziz et al.

(10) Patent No.: US 8,897,853 B2
(45) Date of Patent: Nov. 25, 2014

(54) QUICK-RELEASE SELF-CONTAINED MEDICAL ELECTRODE

(75) Inventors: Mohamed Aziz Ali Mohamed Aziz, Germantown, MD (US); Lee Considine, Towson, MD (US); Artem Dementyev, Rockville, MD (US); Nicholas Olivares, Ellicott City, MD (US); Ayo Adekoya, Silver Spring, MD (US); Jordan Rustad, Ossining, NY (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 13/608,612

(22) Filed: Sep. 10, 2012

(65) Prior Publication Data

US 2013/0172724 A1 Jul. 4, 2013

Related U.S. Application Data

(60) Provisional application No. 61/533,052, filed on Sep. 9, 2011.

(51) Int. Cl.
*A61B 5/0408* (2006.01)
*A61N 1/05* (2006.01)
*A61N 1/04* (2006.01)
*H01R 4/04* (2006.01)
*H01R 43/16* (2006.01)

(52) U.S. Cl.
CPC .......... *A61B 5/04087* (2013.01); *A61N 1/0496* (2013.01); *A61B 2503/045* (2013.01); *H01R 4/04* (2013.01); *H01R 43/16* (2013.01); *A61B 2562/12* (2013.01); *H01R 2201/12* (2013.01)
USPC ............................ 600/391; 607/152; 607/153

(58) Field of Classification Search
CPC ............ A61B 5/0408; A61B 5/04087; A61B 5/0478; A61B 5/0492; A61B 5/6832; A61B 5/6833; A61B 2562/0209; A61N 1/0492; A61N 1/0496
USPC .................. 600/391, 392; 607/149, 152, 153
See application file for complete search history.

(56) References Cited

U.S. PATENT DOCUMENTS

| | | | |
|---|---|---|---|
| 5,961,484 A * | 10/1999 | Gusakov et al. | 604/20 |
| 6,526,303 B1 * | 2/2003 | Scampini | 600/391 |
| 6,952,605 B1 * | 10/2005 | Scarberry | 600/372 |
| 7,269,462 B2 * | 9/2007 | White et al. | 607/153 |
| 7,396,976 B2 * | 7/2008 | Hurwitz et al. | 602/58 |
| 7,532,921 B2 * | 5/2009 | Eichler | 600/372 |
| 2012/0123220 A1 * | 5/2012 | Iyer et al. | 600/300 |
| 2013/0060184 A1 * | 3/2013 | Rea | 602/54 |

\* cited by examiner

*Primary Examiner* — Lee S Cohen
(74) *Attorney, Agent, or Firm* — Rosenberg, Klein & Lee

(57) ABSTRACT

A medical electrode demonstrates a superior adhesiveness to a patient's skin during medical data acquisition or treatment procedure yet attaining painless electrode removal from the skin when needed. The subject medical electrode is designed with adhesive neutralizer (or remover) solvent fully enveloped in one or several compartments embedded in an adhesive layer of the medical electrode unit. The compartments have a contact with the patient's skin when the electrode is attached thereto. When compressed by a medical personnel, the compartment releases the adhesive remover solvent directly to the skin-adhesive interface, thereby neutralizing (or removing) the adhesive material, thereby easing the electrode removal. The adhesive layer is made from PEO, sodium chloride, and water. The adhesive remover solvent contains isopropyl alcohol. A method of manufacturing the medical electrode is presented.

16 Claims, 7 Drawing Sheets

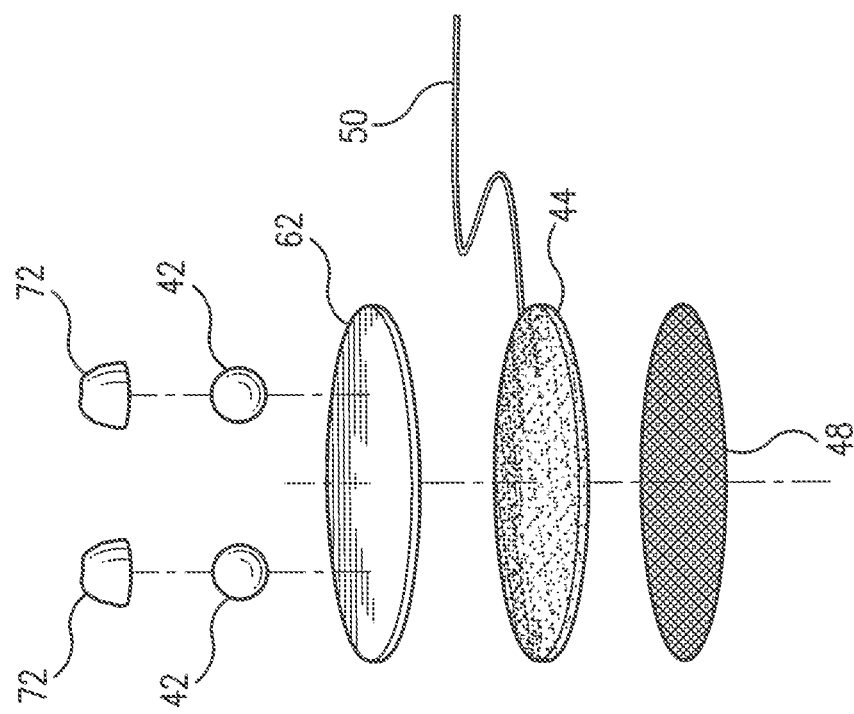

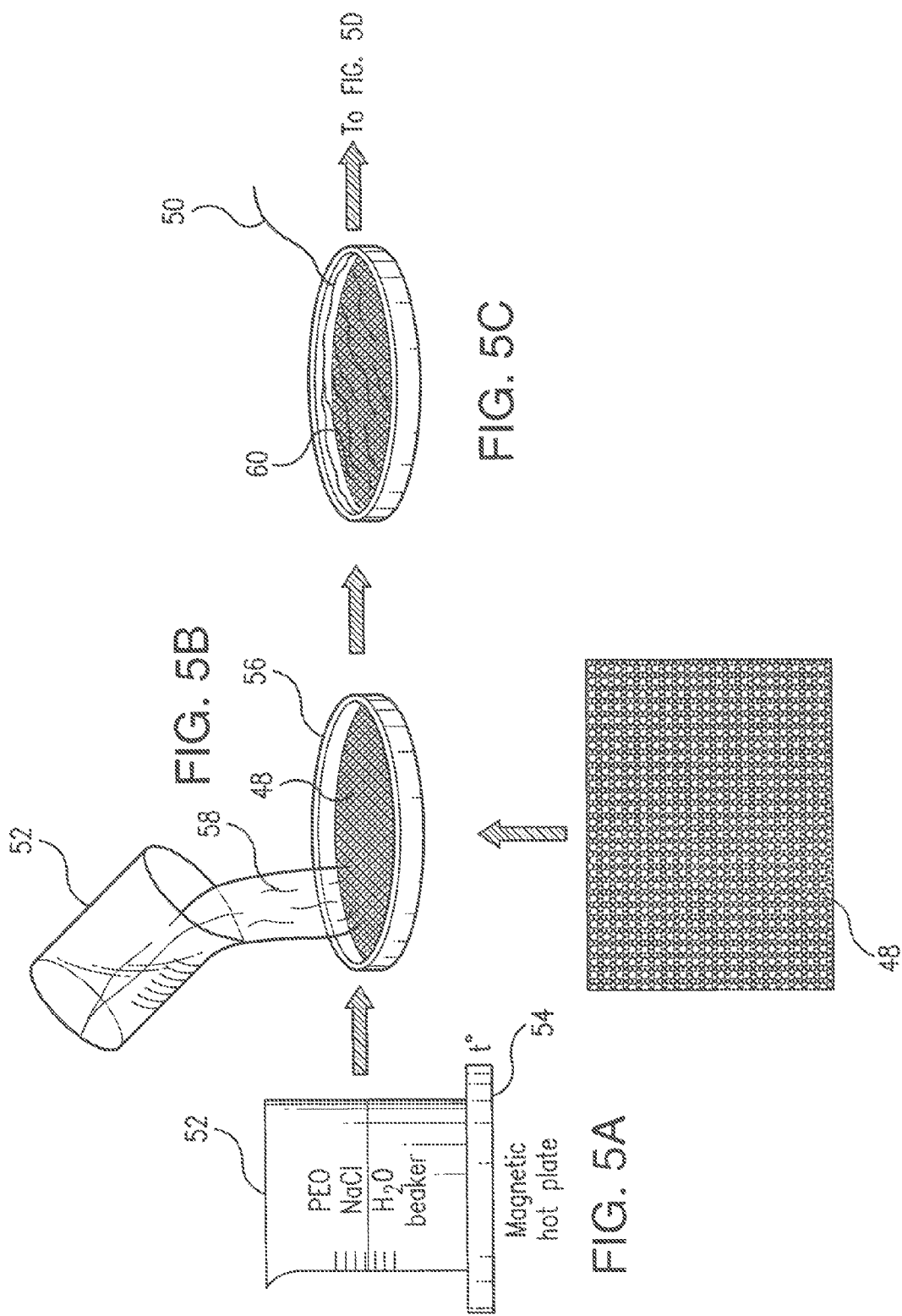

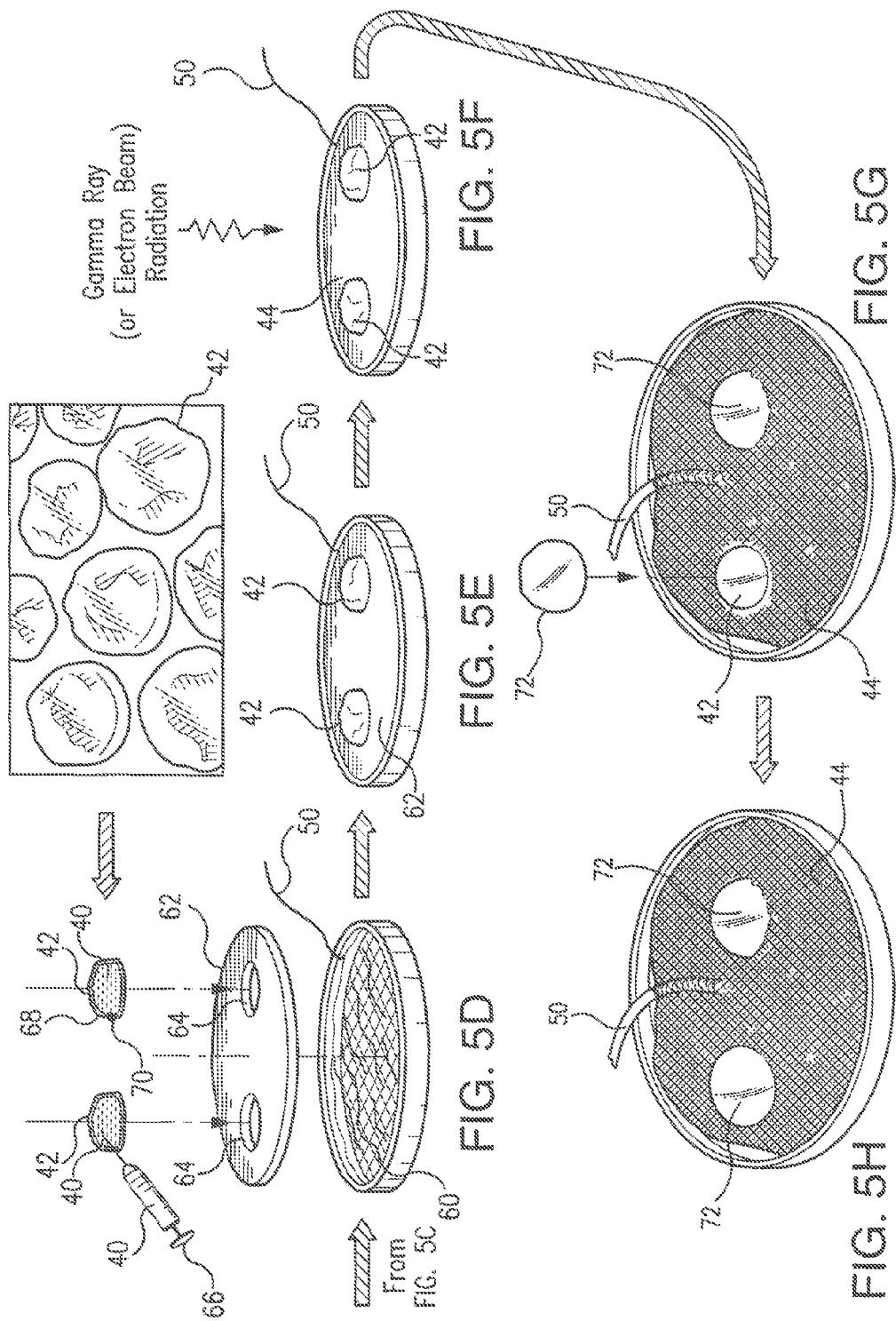

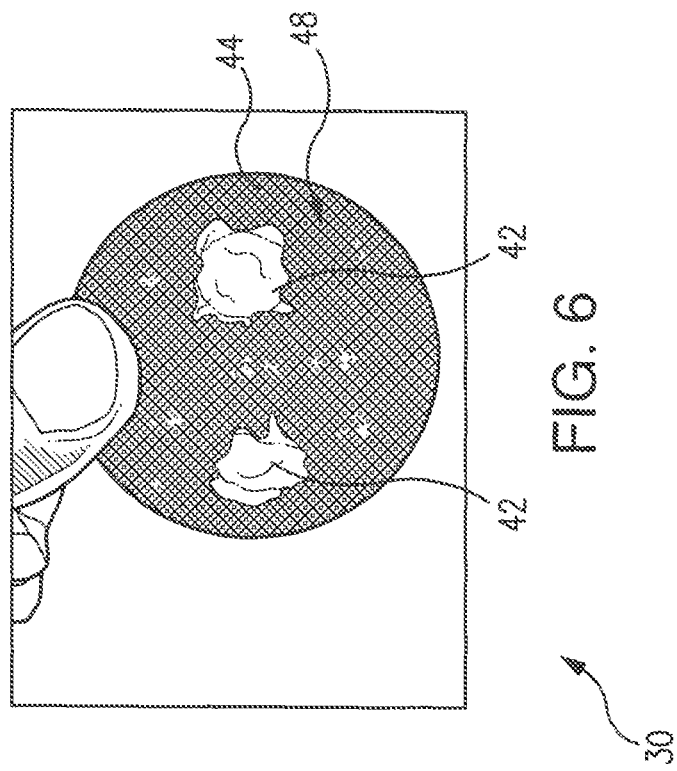

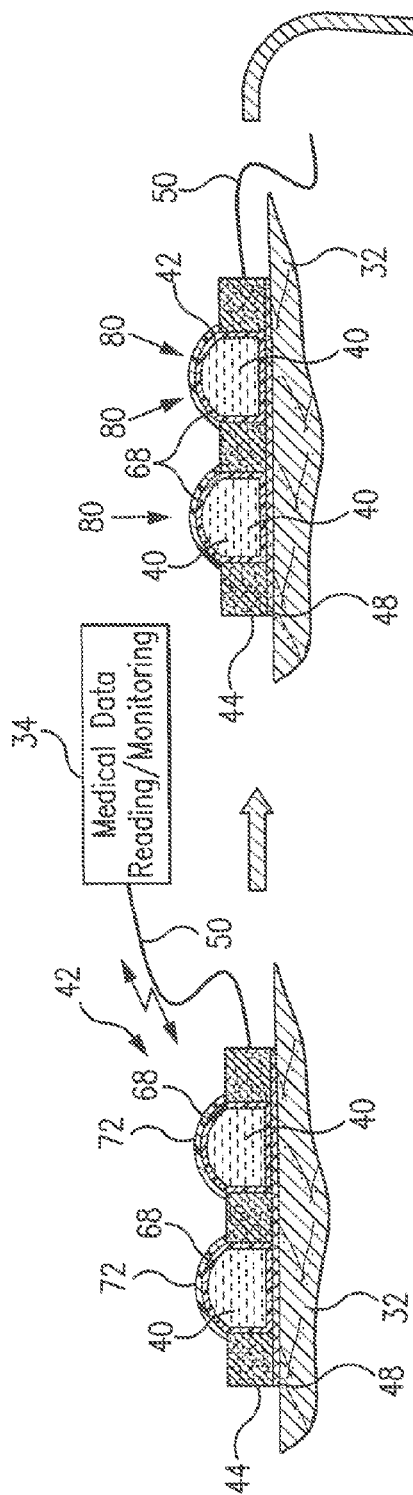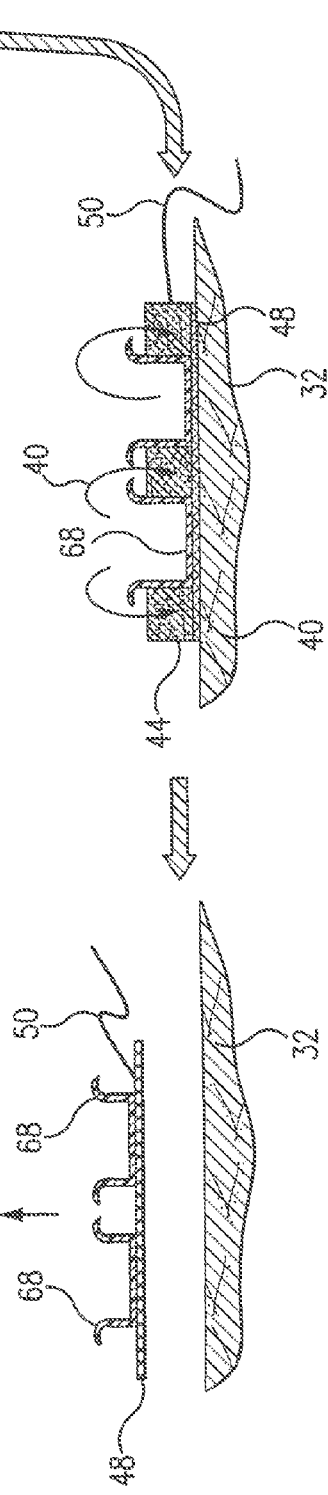

QUICK-RELEASE SELF-CONTAINED MEDICAL ELECTRODE

REFERENCE TO RELATED APPLICATIONS

This Utility patent application is based on the Provisional Patent Application No. 61/533,052 filed on 9 Sep. 2011.

FIELD OF THE INVENTION

The present invention relates to medical devices, and particularly to medical electrodes attachable to a patient's skin.

Even more in particular, the present invention relates to a medical electrode which may be especially beneficial to patients with sensitive skin, such as, for example, neonatal patients, burn victims, and patients with skin rashes, to permit simple and painless removal of the medical electrode upon the electrode's function having been fulfilled.

In overall concept, the present invention is directed to adhesive medical electrodes which can remain on the skin of a patient through adhesion between the electrode and the patient's skin sufficient to prevent inadvertent detachment of the electrode from the skin. However, when the electrode is to be removed from the skin, the adhesion between the electrode and the skin is neutralized (or weakened) to create favorable conditions for painless removal of the electrode.

In addition, the present invention is directed to a medical electrode with an embedded mechanism for a localized delivery of an adhesive remover (neutralizer) solution directly to the skin-electrode interface to effectively "neutralize" the adhesive forces and thus to attain a simple, expedited, and painless removal of the electrode from the skin. The mechanism in question contains an envelope, or a pouch, filled with an adhesive remover (or neutralizer) solvent integrally embedded in the adhesive layer, so that the solvent is supplied directly to the adhesive-skin interface upon the pouch being broken by a compression force applied thereto by a medical personnel. The adhesive, being exposed to the action of the adhesive remover solvent, looses its adhesive force and is removed from the adhesive-skin interface, thereby permitting a comfortable and painless removal of the electrode.

The present invention also is directed to a medical electrode which includes an electrically conductive adhesive layer, adhesive remover, and wire connector integrally interconnected into a flexible and ergonomically viable sheet-like electrode unit which is inexpensive to manufacture and effective in use.

BACKGROUND OF THE INVENTION

Medical electrodes are devices used to transfer the energy of ionic currents in the body into electrical currents which can be amplified, studied, and used in diagnostics. Medical electrodes permit surface quantification of internal ionic currents, yielding a customarily non-invasive test for a variety of nervous, muscular, ocular, cardiac, and other disorders that might otherwise have required surgical intervention to verify their presence. For instance, heart exams using medical electrodes may produce evidence of diminished myocardium strength and may discriminate between primary heart disorders and neurologically-based disorders in addition to detecting heart problems.

Medical electrodes are required to be easy to use, fairly cheap, disposable (or easily sterilizable). In come cases it is beneficial to use electrodes unique to the task they are to perform. The essential role of the electrode is to provide a sufficient electrical contact between a patient's skin and the apparatus used to measure, record, or monitor activity.

Currently, there are disadvantages associated with medical electrodes that are used for cardiac monitoring of hospital patients. One of the major concerns for ECG electrodes is unanticipated detachment. This is extremely dangerous with patients that are in critical care and need remote monitoring to ensure proper functioning of the heart. Inadvertent detachment usually occurs due to a low adhesive strength of the electrodes.

Another contributing factor to unwanted detachment of the electrode is a detrimental characteristic of the skin surface. For example, for some patients, the surface of their skin may be covered with an abundance of hair that may cause improper attachment of the electrode. In other cases, the surface of the skin may be covered with various forms of dirt which also may cause an insufficient adhesive attachment force. These cases require either shaving the hair or cleaning the surface of the skin which is time and labor consuming for medical personnel. In addition, in some cases, for example, for burn victims shaving and/or cleaning is not an acceptable practice.

Another shortcoming of current electrodes is a problem associated with electrodes removal.

The current medical electrodes usually use an adhesive remover solvent to remove or neutralize the adhesive material which is either pre-formed at the bottom surface of the electrode or has to be applied by hospital personnel in a separate action prior to the electrode being attached to the skin.

A major issue that needs to be attended to is pain which may be experienced by a patient as the electrode is being removed. This factor may either be due to high adhesive strength of the electrode, or to the skin sensitivity, and/or hair on the skin surface or a combination thereof. Removal pain is a usual complaint that medical personnel receive from patients during vital signs monitoring involving the use of medical electrodes.

In addition, large amounts of adhesive material may undesirably leave a sticky residue on the skin.

When the electrode is to be removed, an adhesive remover solvent must be obtained and spread around and underneath the electrode for painless detachment. This process is time consuming and difficult for the medical personnel. Many hospitals do not use these solvents, and merely pull the electrodes from the surface of the skin.

In the search for satisfactory medical electrodes, medical and scientific communities have developed a number of designs currently available in the marketplace as well as presenting various designs in numerous publications and patent literature.

For example, a latex-free conductive adhesive electrode Plia-Cell® is manufactured by ConMed Corporation. The electrode is built with a latex free low-profile soft cloth with a radio-translucent snap in the middle of the electrode. The electrode possesses MRI compatibility and can be maintained for a relatively long period of time on the patient's skin.

The ConMed-Plia-Cell® is a solid gel electrode, which is designed with a conductive hydrogel substitute possessing adhesive properties to attain an improved electro-conductive skin-interface contact. The skin-interface substrate of the ConMed-Plia-Cell® electrodes provides pressure sensitive adhesive properties which enable the electrode to adhere to the skin without the use of tape or other securing mediums customarily used with wet adhesive electrodes. The conductive hydrogel substrate substantially eliminates the need for an electrolyte solution, electrode paste or electrode gel.

One of the biggest challenges however experienced with these electrodes, is a low level of tack they can provide. As a result, high pressure must generally be applied to the skin when the electrode is secured in place on a patient's skin, which is undesirable where the patient has sensitive or burnt skin. Another shortcoming of these electrodes is a noticeable amount of a residue adhesive material left on the skin after the electrode removal.

Another type of electrode used currently is the Invisatrace® Wet Gel ECG Electrode, in which an electrically conductive region is designed as a radio-translucent carbon snap. Wet gel electrodes are usually used for long signals and stable baselines. Electrodes, such as the Invisatrace®, achieve a fast electrical contact due to the rapid "wetting" of the skin.

Since this electrode uses a wet gel, the Clear Neoderm® tape is customarily used in order to secure the electrode in place. The wet gel contains water, thickener, ionic salts, surfactants and bactericide/fungicides. To avoid smearing and to reduce motion artifacts, the gel is usually contained in a sponge.

Single gel layer electrode, such as the Invisatrace® Wet Gel electrode and the ConMed-Plia-Cell® are known to compromise the adhesion of the electrode to the skin resulting in a high noise level in the electrical signal being transmitted.

An UltraStim Multistick® electrode manufactured by Axelgaard Corporation is a solid gel type of electrode available with a MultiStick® 2-layer adhesive gel that eliminates performance problems associated with single layer gels. The addition of an intermediate layer permits improved adhesion and increases the reusability potential of the electrode. These electrodes however are costly, and the removal of the electrodes from the skin remains a disadvantage.

The limitations of current electrodes on the market are quite evident due to patients and hospitals' employees dissatisfaction rating.

A number of medical electrodes issues have been investigated and some solutions have been found for the shortcomings of currently available electrodes. For example, Huigen, et al. in *"Investigation into the origin of the noise of surface electrodes," Medical and Biological Engineering and Computing*, Volume 40, Number 3, May 2002, explores the causes of noise while recording biomedical signals with medical electrodes.

This article suggests that increasing the surface area of the electrode will reduce noise and thus will produce a more reliable recording. However, with currently used electrodes, the increase in surface area results in an increase in adhesive in contact with the skin. Removing a larger electrode may be more painful for the patient unless adhesive remover is used.

U.S. Pat. No. 4,706,680 describes a specific adhesive for the medical electrodes that is composed primarily of water and cross-linked polyethylene oxide in a hydrophilic gel.

U.S. Pat. No. 7,252,792 discusses the electrical aspects of medical electrode composition and adhesives to ensure the functional reliability when used to take bio-medical measurements. It is suggested that the electrodes should have uniform conductivities with stable current densities.

U.S. Pat. No. 4,640,289 provides a method to manufacture disposable medical electrodes, and is mainly concerned with the terminal piece which attaches to the ECG lead. The reference discusses the use of electrically conductive adhesive hydrogels instead of conventional electrolyte gels and creams.

U.S. Pat. No. 4,657,023 describes a medical electrode in which the metal terminal is eliminated. In this electrode, an integral centrally located section of the conductive member is directly connected to the ECG lead with a clip.

U.S. Pat. No. 4,842,768 describes a novel electrically conductive gel adhesive. The reference provides examples of a synthesized gel, however, the synthesized gels are not tested for adhesiveness and the reference does not fully address the conductivity issue.

U.S. Pat. No. 5,215,087 proposes a modified design of an electrode with a slightly rounded rectangular shape. The electrode does not have a snap on the connector but uses a tab containing a conductive material. The ECG lead wires are connected to the tab. The electrode uses an adhesive hydrogel made from Acrylic acid and potassium chloride.

U.S. Pat. No. 5,385,679 provides a solid state conductive polymer composition useful in the packaging processes presently required for biomedical electrodes.

U.S. Pat. No. 5,406,945 discloses a disposable biomedical electrode formed with an electrolytic gel which decreases the pain and experienced when tearing hair from the patient's body. The hydrogel material is formed from an aqueous material of polyhydric alcohol. Other materials which reduce discomfort to the patient would include polyethylene oxide based polyamine and sodium chloride.

U.S. Pat. No. 7,346,380 discloses a medical electrode that is suitable for both stimulation and monitoring applications. This medical electrode includes an electrically conductive member capable of being connected to an external electromedical apparatus. This member is in the form of a pliable sheet formed from a material that comprises organic polymer plasticized with a polyhydric alcohol. The polymerization of acrylic acid and N-vinylpurrolidone is used for the copolymer of the adhesive of this medical electrode.

U.S. Pat. No. 5,961,484 describes a medical electrode which includes an external applicator filled with an adhesive remover. As shown in FIG. 1, the electrode comprises a flexible planar member 10 which faces the skin 12 of a patient, and an electrically conductive member 14 embedded in the planar member 10. Electrical wires are attached between a stud 16 and a medical data acquisition device 18. The electrode includes an electrically conductive adhesive 20 which is placed on the side of the planar member 10 which faces the skin of the patient. The electrically conductive adhesive 20 assures that the electrode remains in place on the patient's skin.

Through holes 22 are formed in multiple locations throughout the planar member 10, and alternatively may be formed through the conductive adhesive 20.

An applicator 24 comprising absorbent dispensing material 26 which contains a solvent or adhesive-neutralizing material is attached on the top of the planar member 10. The dispensing material 26 comprises a sponge or cloth material, or a foam which is saturated with the adhesive-neutralizing solvent. Dispensing material 26 is surrounded partly with a thin flexible plastic layer 28. By applying pressure in the direction of arrow R (shown in FIG. 1) on the top of the applicator 24, a user forces the solvent through the holes 22 toward to interface between the adhesive 20 and the skin 12. In this manner a less painful electrode removal from a patient's skin may be achieved.

This design is costly in its fabrication. In addition, the applicator requires accurate measurements of its mechanics, and the manufacturing process requires additional operations for formation of passages for the adhesive remover through the planar member and the adhesive layer. Additionally, due to its viscosity, the adhesive material cannot maintain the holes in an open configuration. Thus, the passage of the solvent to the electrode-skin interface may be obstructed, thereby undermining the intended functionality of the electrode.

Despite rather extended searches in the area of medical electrodes, there is still a long-lasting need for an ergonomically viable medical electrode which would be reliably attachable to, and yet easily and painlessly removable from skin, as well as being inexpensive to manufacture for convenient use by a medical personnel.

SUMMARY OF THE INVENTION

It is therefore an object of the present invention to provide a medical electrode designed especially for patients with sensitive skin to decrease (or eliminate completely) the pain experienced by the patients when the electrode is removed.

It is another object of the present invention to provide a medical electrode having increased adhesive strength for reliable and prolonged attachment to the skin of the patient in order to prevent inadvertent detachment from the patient's skin, thus decreasing the probability of false readings of cardiac signals and/or other measured and monitored patient's conditions.

It is further an object of the present invention to provide a medical electrode in which the electrode and the adhesive remover solvent are integrated in a single unit for ergonomic purposes and convenience in usage by a medical personnel.

One of the major objects of the present invention is to provide a medical electrode which attains a decreased level of pain experienced by a patient when the electrode is removed. This object is attained through an adhesive remover delivery mechanism embedded into the electrode unit for the localized delivery of the adhesive remover solvent directly to the adhesive/skin interface. The unique solvent delivery system provides an effective dissolution (neutralization) of the adhesive "glued" (attached) to the patient's skin.

A further object of the present invention is to provide a medical electrode demonstrating a decreased amount of leftover residue of the adhesive on a patient's skin through the efficient supply of the adhesive remover solvent directly to the adhesive-skin interface.

In one aspect, the present invention represents an adhesive medical electrode structure which includes a medical electrode unit attachable to a patient's skin through the use of an adhesive layer disposed at the bottom of the electrode unit and facing the patient's skin.

When attached to the skin, the electrode forms an adhesive-skin interface through which electrical current passes, to be transmitted in the form of signals, to an external medical monitoring, or data acquisition equipment. The adhesive layer is formed with electrically conductive properties, thus wire connectors are attached directly to the electrically conductive adhesive layer.

The adhesive material preferably is a hydrogel material containing polyethylene oxide (PEO), sodium chloride, and water. The hydrogel material may contain 6%-10 weight % of PEO, 5%-8 weight % of sodium chloride, and 80%-90 weight % of water, with a preferred content of 10 weight % of PEO, 5 weight % of sodium chloride, and 85 weight % of water. The content of the adhesive material is chosen for attaining a strong adhesion of the electrode to the skin and for obtaining satisfactory electrical properties.

The subject medical electrode unit is fabricated with one or several compartments embedded in the adhesive layer which is in contact with the patient's skin. The compartment(s) is (are) defined by a polymer envelope which is filled with an adhesive remover (neutralizer) solvent. When the polymer envelope is broken, the adhesive remover solvent is released directly on the adhesive and to the adhesive-skin interface. The adhesive material is dissolved thereby providing a comfortable and painless electrode removal from the skin.

The adhesive remover includes isopropyl alcohol or water, or combinations thereof.

A wire connector is coupled at one end thereof, to the electro conductive adhesive hydrogel. The wire connector extends from the electrode to a signal receiving medical device and is coupled thereto.

The subject medical electrode may include a non-conductive mesh grid underlying the adhesive layer for structural integrity.

Additionally, a non-conductive material, such as, for example, Gore-Tex® fabric, may be used atop the adhesive hydrogel layer in surrounding relationship with the compartment(s) filled with the adhesive remover solvent.

A medication, for example, an antibiotic, may be added into the compartment(s), and/or in the adhesive layer.

Each compartment may be in the form of a plastic envelope contemplated as a plastic bubble (such as in a plastic bubble wrap), with each bubble serving as the compartment. The bubbles are filled with the adhesive remover solvent, and the filling puncture in the bubble membrane may be sealed with a "glue", to form an impermeable membrane to prevent the solvent from inadvertently escaping from the bubble. A single or several bubbles filled with the adhesive remover solvent are envisioned for each electrode unit.

In another aspect, the present invention is a method of attaching a medical electrode to a patient's skin and for subsequent removal of the subject medical electrode therefrom. The method comprises the steps of:
  forming a medical electrode unit including:
  an electrically conductive adhesive layer,
  an adhesive remover solvent filled in at least one compartment embedded in the adhesive layer and completely surrounding the adhesive remover solvent within the compartment's envelope, and
  at least one electrical connector coupled to and extending from the electrically conductive adhesive layer, where the adhesive layer, adhesive remover solvent, and electrical connector are integrally joined in the medical electrode unit.

The method further comprises the steps of:
  attaching the medical electrode unit to the patient's skin through the adhesive layer applied to the patient's skin so that the compartment's envelope is in direct contact with the skin,
  connecting the electrical connector to an external medical device for bio-medical data acquisition, and
  upon performing the readings of the patient's bio-medical data breaking the compartment's envelope filled with the adhesive remover solvent, thereby releasing the adhesive remover (neutralizer) solvent directly to the adhesive layer at the adhesive-skin interface to dissolve (neutralize) the adhesive material, thereby weakening the adhesive force between the electrode and the skin, and
  removing the medical electrode while minimizing the pain caused by the removal process.

The impermeable envelope surrounding the adhesive remover solvent may be broken by application of a compressing force applied by medical personnel.

Another aspect of the present invention covers a method of forming a medical electrode, comprising the steps of:
  combining PEO, NaCl and water in predetermined proportions,
  preparing a non-conductive mesh grid sheet,
  covering the combination of PEO, NaCl and water on the mesh grid sheet, thus forming an electrically conductive adhesive layer intermixed with the filaments of the mesh grid sheet, and attaching a wire connector to the formed adhesive layer.

In the subject method, the adhesive layer is preferably produced from a material containing approximately 10% wt. of polyethylene oxide, 5% wt. of sodium oxide, and 5% wt. of water, which is subjected to cross-linking high energy irradiation.

The wire connector is intended for connection to an external medical device of interest. The wire connector may be replaced with a telemetric transmitter or transceiver to transmit signals to the external medical equipment.

The method continues with the step of cutting-out openings in a sheet of Gore-Tex®, filling the bubbles with an adhesive remover (preferably, the isopropyl alcohol), and sealing the rupture point in the non-plastic membrane of the bubble, thereby fully enveloping the adhesive remover within the non-permeable membrane.

Subsequently, embedding the bubbles filled with the adhesive remover solvent in the cut-outs made in the GoreTex® sheet, and attaching the Gore-Tex® layer with the bubbles to the top of the hydrogel.

The structure is exposed to the gamma ray or electron beam irradiation, resulting in a strong hydrogel adhesive layer integrally solidified with the bubbles embedded therein and the wire connector attached thereto. During the irradiation, the bubbles "sink" into the hydrogel towards the mesh grid and remain integrated into the hydrogel adhesive.

The bubbles are further covered with resin covers for protection, which additionally serve as indicia of bubbles location for the medical personnel.

These and other features and advantages of the present invention will be apparent from the following detailed description taken in conjunction with accompanying Patent Drawings.

BRIEF DESCRIPTION OF THE DRAWINGS

FIG. 4 is exploded view of the medical electrode of the present invention;

FIGS. 5A-5H represent schematically the sequence of operations for manufacturing the medical electrode of the present invention;

FIG. 6 is a bottom view of the subject medical electrode; and

FIGS. 7A-7D represent schematically a sequence of steps for attachment to and subsequent removal of the present medical electrode from the skin of a patient.

DETAILED DESCRIPTION OF THE PREFERRED EMBODIMENT

Referring to FIGS. 2-4, and 6, a medical electrode 30 of the present invention is an electrode which is attached to a patient's skin 32 and is electrically connected to an appropriate medical electrical device 34, such as for example, a biomedical data acquisition device, an ECG, medical monitoring device, electro-stimulator equipment, or the like.

The medical electrode 30, intermittently referred to herein as the medical electrode unit, includes an electrode body 36 made from a non-conductive flexible breathable, water-proof material providing structural support and integrity to the entire electrode unit and its parts. As an example, Gore-Tex® may be used for the electrode body 36 to provide structural support to the entire electrode unit.

The electrode body 36 is shaped to embed one or more compartment(s) 38 filled with an adhesive remover (neutralizer) 40. Although shown in FIG. 2 as somewhat of a circular shape, any other shape including square, rectangular, oblong, etc. is also applicable in the subject electrode body 36.

Figure 1:
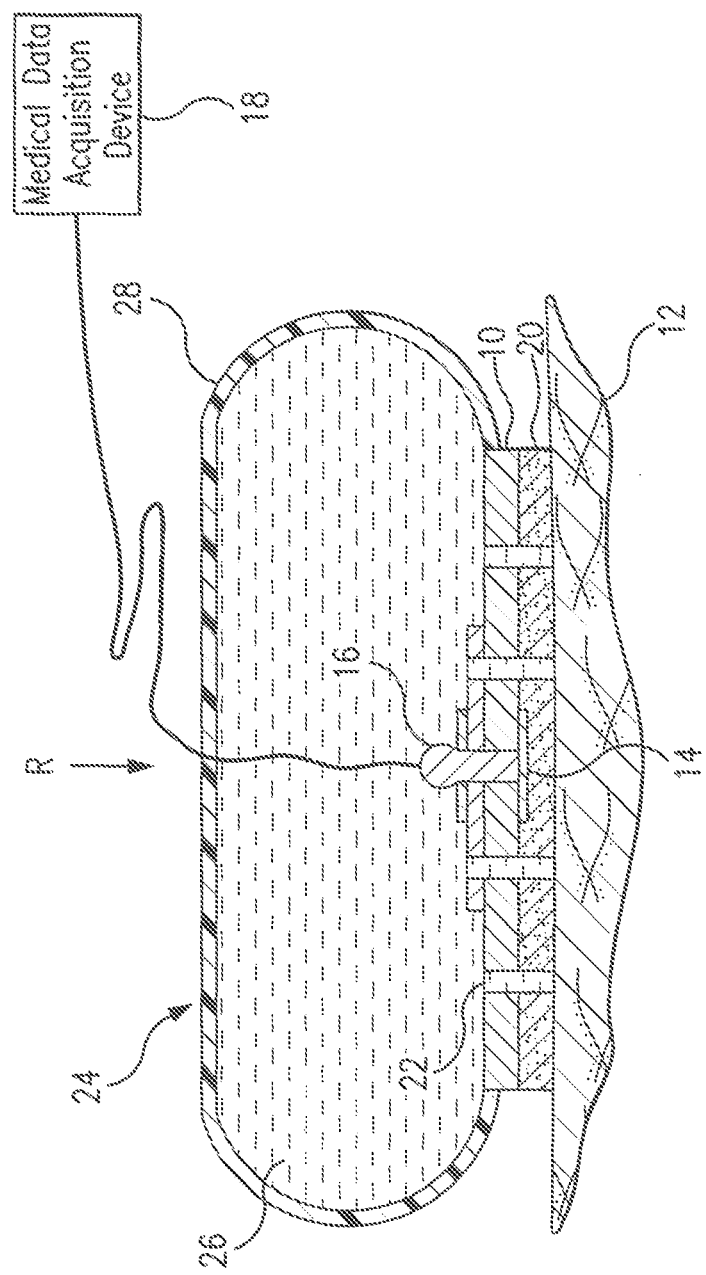
FIG. 1 is a schematic representation of a medical electrode of the prior art.
Figure 2:
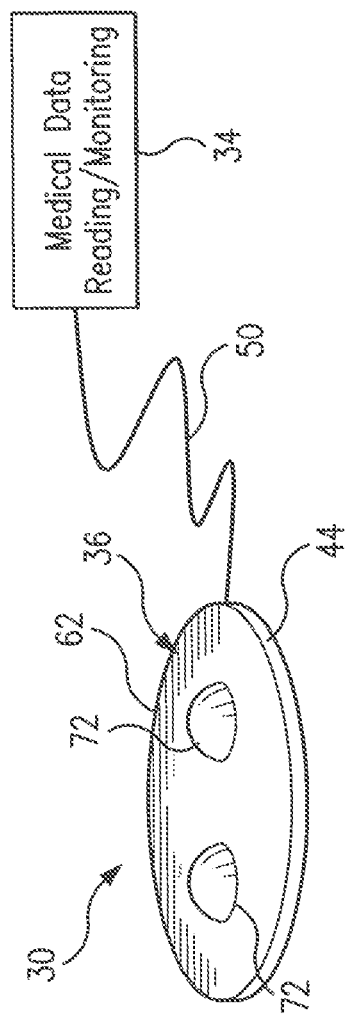
FIG. 2 is a prospective view of the medical electrode of the present invention.
Figure 3:
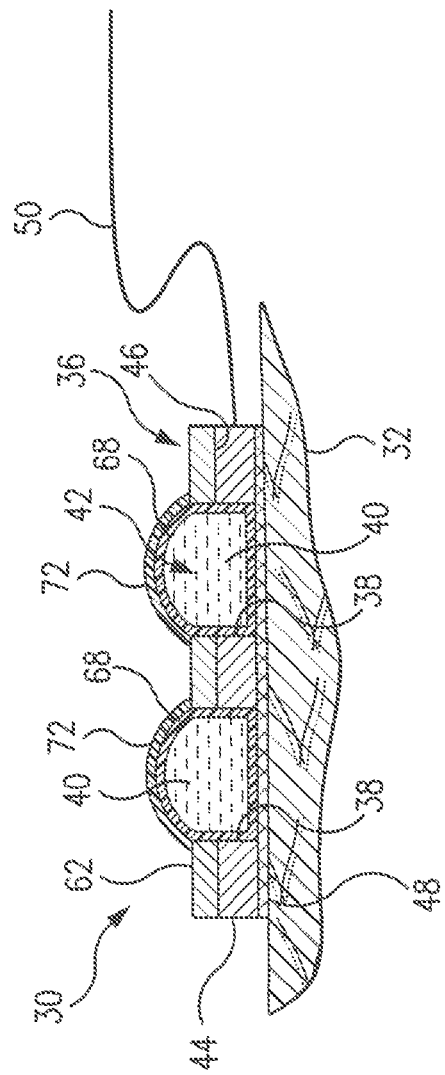
FIG. 3 is a cross-section of the medical electrode shown in FIG. 2.

The design of the subject medical electrode, as an example, may use a plastic bubble wrap whose bubbles 42 are incorporated on the design to serve as compartments 38 filled with the adhesive remover solvent 40. Although the medical electrode unit 30, as shown in FIG. 3, contains two compartments 38, a single or any other number of compartments is (are) contemplated in the design of the subject medical electrode. Therefore, one or several bubbles 42 may be used in the electrode unit 30 for enveloping the adhesive remover solvent 40.

The adhesive remover solvent 40 is inserted into the bubbles 42, for example, with a syringe. An area of penetration of the syringe needle is sealed, for example, with hot silicon glue, in order to provide an impermeable envelope completely surrounding the adhesive remover solvent 40.

An electrically conductive adhesive layer 44 is attached to the lower side 46 of the electrode body 36. The electrically conductive adhesive layer 44 assures that the medical electrode unit 30 remains in place on the patient's skin 32 and provides the required electrical conductivity between the patient's skin and the conducting plate 46 for data acquisition, or other biomedical purposes.

A plastic mesh 48, or any other appropriate sheet material, may be positioned underneath the conductive hydrogel layer 44 to underlie the entire electrode unit structure in order to enhance its structural characteristics and prevent it from deformation and stretching when used on an individual. The adhesive material may penetrate the mesh to intermix with the filaments of the mesh grid 48.

In the electrode 30, the bubbles 42 are embedded into the hydrogel layer 44 and are exposed at the bottom of the electrode unit 30, as shown in FIGS. 3 and 6, in order to provide a direct contact with the patient's skin.

A wire connector 50 is attached to the electrode unit 30 (specifically to the conductive hydrogel layer 44), in order to conduct biomedical electrical signals of interest to (or from) the medical data acquisition device 34.

Although a wire connection is shown between the electrode unit 30 and the medical data acquisition device 34, a telemetric data transmission is also contemplated in the scope of the present invention which would include, instead of wires, a transmitter (or transceiver) at the medical electrode unit 30 which transmits data to the medical data acquisition device 34 which for this purpose is equipped with a receiver (or transceiver) for receiving the transmitted data.

The adhesive layer 44 is formed from an electrically conductive hydrogel. The conductive hydrogel used for the adhesive layer in the present device is characterized by a surface stickiness and a cohesiveness sufficient to maintain structural integrity of the adhesive layer when being removed from the skin. In addition, bio-compatibility of the adhesive layer is an important characteristic of the material. The adhesive material applicable in the medical electrode is inert, non-metabolizing, and hypoallergenic.

The content of the adhesive includes polyethylene oxide, sodium chloride, and water which are present in the material in the approximate ranges of 6-10 weight % of polyethylene oxide, 5-8 weight % of sodium chloride, and 80-90 weight % of water.

The preferred content of ingredients in the adhesive material is 10 weight % of polyethylene oxide, 5 weight % of sodium chloride, and 85 weight % of water.

The hydrogel in the suggested combination provides the flexibility and bio-compatibility needed for skin applications as well as adhesion strength which is stronger than the current electrodes on the market. The polyethylene oxide is used in the adhesive material as a polymer matrix to provide an adequate viscosity.

The hydrogel's adhesiveness depends on its ability to conform to minute irregularities on the skin surface and to retain its cohesive properties. The hydrogel in the subject medical electrode remains adhesive even while absorbing skin perspiration. The hydrogel, due to its viscostatic characteristics, provides a strong contagious contact with the skin.

The NaCl in the hydrogel is included to increase the ability of the hydrogel to carry electrical current, so that the electrode is able to detect sensitive electrical pulses from the heart ECG, the brain EEG signals, and the like.

The sodium chloride salt component provides electrical conductance for the medical electrode to be used effectively with medical data acquisition equipment. Sodium chloride is an agent which provides electrical transmission between the human body surface and the medical data acquisition and monitoring equipment. Therefore, it is important to maintain a constant percentage of the sodium chloride in the adhesive.

Water is an important component and the highest percentage component of the hydrogel in question. This component maintains the adherence level of the hydrogel as well as serving as the hydrating agent to maintain the hydrating characteristics at the interface between the patient's skin and the medical electrode. The high water content additionally precludes the necessity of preparatory skin shaving.

The water is an integral unseparable part of the hydrogel structure. For this reason the hydrogel remains a homogeneous composition. The hydrogel cleans the body surface of water soluble exudates and secretions through osmosis, thus preventing the skin irritation. The hydrogel layer is flexible, conforms to the irregularities of skin, and thus produces a substantially uniform contact therewith, thus lowering probability of excessive electrical noise or current loss which can undermine the accuracy of a medical data recording and efficiency of any possible treatment.

Since the hydrogel sheet or film is produced with high energy radiation, such as that produced by an electron accelerator, it is sterile.

Referring to FIGS. 4, and 5A-5H which schematically represent the sequence of the operations used for manufacturing the medical electrode of the present invention, the process is initiated with fabrication of the electrically conductive hydrogel.

As presented in FIG. 5A, the hydrogel conductive sheet suitable for use in the subject medical electrode may be produced by mixing the water soluble linear polyethylene oxide (PEO) with the selected salt (NaCl) and water to form a viscous feed. The polymer is gradually blended into the solution of NaCl in the beaker 52 over a magnetic hot plate 54. Blending also could be performed at ambient temperature. The mixture is mixed for about 1-3 minutes at the speed of up to 5 rpm.

As further shown in FIG. 5B, a plastic mesh grid 48 is pre-cut and placed on the bottom of a Petri dish 56. The viscous liquid feed 58 from the beaker 52 is then uploaded into the Petri dish 56 to cover the mesh 48 thereby forming a liquid film 60 thereon. Polyethylene also penetrates between and is intermixed with the filaments of the mesh. Although it is possible to form the subject electrode without the mesh, the mesh 48 contributes to the strength of the hydrogel both in tension and flexure. The mesh grid is preferably fabricated from a natural or synthetic hydrophobic polymer, e.g., a polyethylene, polypropylene, polyester, or polyamide homopolymer. The mesh grid is described herein as one of the examples of structural supporting material. Other non-conductive flexible sheet-like materials may also be used for these purposes.

Further, as shown in FIG. 5C, one end of a wire connector 50 is placed into the liquid hydrogel 60. Further, as shown in FIG. 5D, a Gore-Tex® sheet 62 is cut to correspond to the shape and size of the Petri dish. The GoreTex® is a non-conductive impermeable material and can provide suitable attachment to the hydrogel adhesive layer 44. Openings 64 are cut out in the Gore-Tex® sheet 62 to receive bubbles 42 therein. Each bubble 42 is filled with the adhesive remover solvent 40, for example, 91-92% isopropyl alcohol or water.

Approximately 1 ml of the solvent 40 is filled in each bubble 42 by a syringe 66. Care is taken to avoid air passage into the bubbles. A puncture point left by the syringe in each bubble is then glued by hot silicon 70 to ensure impermeability of the bubble's envelope (membrane) 68.

The dimensions of the bubbles 42 may be in the range of approximately 1 cm in diameter and ½ cm in height.

Further, as shown in FIG. 5E, the Gore-Tex® sheet with the bubbles 42 embedded therein, is lowered onto the surface of the liquid hydrogel 60.

In a further step, shown in FIG. 5F, the contents of the Petri dish 56 are exposed to the gamma ray radiation, or, alternatively, to electron beam irradiation, where the liquid hydrogel 60 is converted into a solid hydrogel 44. The energy dose may be approximately 0.67 microradian. During this step, the contact between the wire 52 and the hydrogel 44 is solidified. After the conductive hydrogel sheet 60 is irradiated and converted into a viscoelastic solid layer 44, it serves as an adhesive layer in the subject electrode 30. If the mesh is used in the manufacturing process, the hydrogel also is viscoelastically solidified between the filaments of the mesh.

The radiation applied not only solidifies the gel, and promotes the intermixture of the hydrogel with the mesh, it also causes the bubbles 42 to sink into the hydrogel material as shown in FIGS. 3, 6, and 7A-7B. This step facilitates integration of all parts of the electrode into a single integral unit.

Further, as shown in FIGS. 5G and 5H, resin protecting members 72 are covered on the bubbles 42 to serve both as a protective mechanism for the thin membrane 68 of the bubbles 42 as well as indicia for medical personnel to determine the location of the bubbles when the structure shown in FIG. 5H is packaged.

The electrode prototype shown in FIG. 5H is then ready to be sterile packaged. The package may be a gas, moisture and microorganism impermeable sealed pouch or envelope, e.g., formed by heat sealing a heat sealable aluminum foil polymer laminate or other like envelope composition.

When the electrode is attached to the skin, the bubbles 42 filled with the adhesive remover 40, as shown in FIG. 3 (being embedded within the conductive hydrogel 44), come in direct contact with the human skin 32. By using compression force, the bubbles 42 may be burst to release the hydrogel adhesive remover solvent 40 directly on the hydrogel and to the interface between the adhesive and the skin of the patient, as will be further described in conjunction with FIGS. 7A-7D.

The adhesive remover solvent used in the present electrode contains about 91% isopropyl alcohol which fills a full volume of the bubbles (or any other compartment embedded in the electrode unit). On average, it takes about 1 minute to remove the adhesive from the skin under the electrode unit.

It is contemplated in the scope of the present invention that a medication, such as for example an antibiotic, can be added to the hydrogel layer 44 or injected into the bubbles 42, in order to provide benefit for the people with skin wounds such as, for example, burn victims.

The current design of the medical electrode 30 is the result of extended studies and tests performed to result in the adhesive electrical, mechanical and diffusion properties of the materials applicable in the subject medical electrode. Overall results of individual tests exhibited the following results:

Adhesion Properties

Optimal PEO by weight is 6%-10% to achieve a stronger adhesion than is exhibited in commercial hydrogel based electrodes.

To determine how PEO content affects adhesion of hydrogels and to compare synthesized hydrogels with existing commercial products, the adhesion was tested by Tack Rolling Ball Test, which is ASTM D3121 Standard. The testing apparatus consisted of an inclined track and a steel ball. The inclined track was angled at 23.6 degrees and 6 inches long. 21.7 gram stainless steel ball was used. Apparatus was constructed from aluminum.

The test apparatus was placed on flat surface. Hydrogel was placed at the end of the track. The ball, hydrogel and the track were thoroughly cleaned with alcohol. The ball was released from the top of the inclined track. At the end of the track, the ball encountered a flat piece of hydrogel which terminated the ball displacement. Distance from the end of the track to the first edge of the ball was measured. The ball was cleaned with isopropyl alcohol after each run. Sterile gloves were used to handle the ball. Each sample was tested five times and the average was taken.

Results:

Adhesiveness appears to be highly dependent on the content of PEO in the hydrogel. The general trend showed that adhesiveness increases with increasing concentration of PEO in the hydrogel.

The results of the test showed that 6%-10% PEO formulation provided optimization in adhesiveness and ease of manufacturing. 4% PEO gave 33.6 mm travel distance, which is greater than any other samples, including commercial products. As a result, 4% was avoided based on its weak adhesiveness. 10% PEO gave the best adhesion, but is found to be difficult to manufacture due to its viscosity. 6% PEO and 8% PEO did not show a significant difference. But, 8% was difficult to manufacture because of its viscosity. Based on this conclusion, 6% PEO was used on the preferred percentage for all later prototypes.

6% PEO is shown to be more adhesive then CVS hydrogel which was used for wound dressing.

Electrical Properties

Resistance of the hydrogel is about 26 Ohms which is substantially better than the literature recommended less than 100 Ohms.

To determine electrical resistance of synthesized hydrogel samples, the electrical resistance was measured by an impedance analyzer. 5 mm×5 mm hydrogel sample was placed in a Teflon® ring, with dimensions of 1 mm thickness, 5 mm inner diameter, and 14 mm outer diameter. The Teflon® ring with the sample was compressed by two stainless steel cylinders. A vise grip was used to hold the cylinders and electrical tape was used to secure the Teflon® ring in place. Samples were tested in the impedance analyzer with frequencies from 1 Hz to 106 Hz. 60 impedance data points were taken at different frequencies. Impedance Z' was graphed in the X-axis versus second impedance Z" in the Y-axis. The resistance value was determined from X-intercept of the resulting graph.

Only 6% PEO samples were tested. As shown in Table 1, two samples (1 and 2) with no mesh were tested. The resistance of the two samples was similar. A third sample had a mesh, taken from CVS wound dressing hydrogel. The third sample showed much lower electrical resistance, than samples with no mesh.

TABLE 1

| Sample | Description | Resistance (Ohms) | Conductance |
|---|---|---|---|
| 1 | No mesh, 6% PEO | 26.7 | 0.00749 |
| 2 | No mesh, 6% PEO | 26.8 | 0.00746 |
| 3 | CVS mesh, 6% PEO | 8.95 | 0.0223 |

Resistance of all samples was consistently less than 100 Ohms, which indicates that synthesized hydrogel is appropriate for picking up electrical bio-signals from muscles or heart.

Mechanical Properties

Maximum breaking pressure of the bubble wrap was determined to be 0.223 MPa which is lower than 0.58 to 3.9 MPa range of commercial capsules.

To determine pressure required to burst bubbles filed with isopropyl alcohol and compare pressure to the values given in literature, an H25KT universal testing machine was used. Bubble wrap was placed in a plastic culture dish. Compressive force was applied to the bubble. A computer monitored the deformation and force on the bubble until the bubble failed. Stress was calculated by using a 10 mm diameter bubble. Strain was calculated by using the 5 mm height of the bubble. Five samples were tested. The bubbles were prepared prior to the testing by injecting isopropyl alcohol into the bubble with a metal medical syringe. Then bubble was sealed with silicone sealant and was left to dry for 24 hours.

Total of five bubble wrap samples were tested as presented in Table 2.

TABLE 2

| Sample | Burst Pressure (MPa) |
|---|---|
| 1 | 0.1273 |
| 2 | 0.223 |
| 3 | 0.0845 |
| 4 | 0.223 |
| 5 | 0.106 |

Diffusion Properties

Very slow diffusion of isopropyl alcohol was determined.

To determine how long it takes for hydrogel to loosen its adhesion based on alcohol diffusion a unique testing procedure was developed. A 12.7 cm×12.7 plate was constructed from plastic. In the middle a 30 mm diameter circular hole was formed. The plate was suspended. A hydrogel sample was placed on top of the hole. On the bottom of the circular hole, a 12.7×12.7 mm piece of pig skin was attached to the hydrogel. A string was used to attach plastic lid (about 2 grams) to the corner of the skin sample. Isopropyl alcohol was poured on top of the hydrogel sample. The time it took for a piece of skin to completely detach from hydrogel was recorded.

Negligible diffusion through the hydrogel was observed. Holes made with medical needle did not increase the diffusion rate. Isopropyl alcohol was able to go through the hydrogel when large incisions (about 3/16 inch long) were made with a scalpel.

The results of the test show that diffusion should not be the mechanism to loosen the adhesive material. The test also showed that holes cannot be simply made in the hydrogel to induce diffusion. Due to elastic behavior or the hydrogel, itself, the holes close. Holes have to be reinforced, to prevent them from closing.

Referring to FIGS. 7A-7D, which is a schematic representation of the sequence of performed steps for attachment to the patient's skin and subsequent removal of the present medical electrode from the skin of the patient, the process is initiated in FIG. 7A with attachment of the electrode 30 to the patient's skin 32 with the adhesive layer 44 directly adhering to the skin. The membrane 68 of the bubble is in contact (through the mesh 48, if used) with the skin 32. Upon attachment to the skin, the communication with an extraneous medical equipment 34 is established, either through the wire connection or through telemetric communication for biomedical signals acquisition.

The electro conductive adhesive layer serves also as a conductive region. In comparison with commercial medical electrodes which rely on a conductive plate on the top of adhesive layer, the present medical electrode attains a stronger signal since its conductive element (hydrogel) is positioned directly on the skin. Moreover, the subject electrode is much simpler than commercially available electrodes since no additional conductive element is needed to be incorporated in its design. The hydrogel layer serves both functions, i.e. adhesive means and conductive means.

Upon the process of data acquisition or electrical treatment being completed, the membrane 68 of the bubbles 42 is broken in FIG. 7B by application of a squeezing or compression force 80, so that the liquid, i.e. the adhesive remover solvent 40, leaks out on the adhesive 44 and neutralizes and/or removes the adhesive material, as shown in FIG. 7C, so that the electrode can easily be removed from the skin, as shown in FIG. 7D, substantially painlessly and with a minimum of discomfort.

The subject medical electrode achieved several goals:

An increased adhesiveness of the hydrogel by creating an electrode with superior adhesive properties as compared with commercially available electrodes.

Integration of the electrode and the adhesive remover into a single unit. By polymerizing the electrode with all of its components (i.e., the electrically conductive hydrogel adhesive, solvent compartments (bubbles), adhesive remover solvent, non-conductive structural enhancing members), the system is convenient to use, ergonomically viable, and easily manufacturable.

The force required for electrode removal from the skin was significantly reduced. By introducing the adhesive remover solvent at the hydrogel-skin interface, the force required to peel the electrode from skin is dramatically reduced.

Leftover residue was eliminated from the patient's skin at the removal of the electrode through developing the adhesive hydrogel which maintains its structural integrity even if the adhesiveness of the hydrogel is compromised by the adhesive remover solvent. This was possible through maximizing the PEO content, and due to the use of a solvent delivery system that directs the remover to the hydrogel-skin interface.

The subject medical electrode is applicable to cases where skin sensitivity is a medical concern. In the case of burn patients who may have either no skin or a newly growing skin in the areas where the electrodes would be adhered, the subject electrode is beneficial in that the removal of the electrode does not compromise the local tissues. The developed electrode unit directs the solvent to the hydrogel-skin interface, therefore dramatically reducing the adhesive strength of the electrode and correspondingly the force required to remove the electrode.

The subject electrode is easy to manufacture and is cost effective. The hydrogel developed, maximizes PEO concentration while still using a concentration that can be handled and molded under normal conditions. This makes it possible to make the hydrogel in a laboratory setting without the use of specialized machinery or extreme time sensitivity. In terms of affordability, the materials used are inexpensive and readily available from a large number of manufacturers. Of the materials used, poly (ethylene oxide) is the most expensive component of the design. The second highest expense is the non-conducting material, such as Gore-Tex®. Gore-Tex® may be substituted for with any inexpensive, non-conducting, impermeable fabric.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of the elements may be reversed or interposed, all without departing from the spirit or scope of the invention as defined in the appended claims.

What is being claimed is:

1. A medical electrode unit adapted to be in contact with a patient's skin, comprising:
   a medical electrode including:
   an electrically conductive hydrogel adhesive layer;
   a non-conductive mesh grid formed with filaments and positioned underneath said adhesive layer, and interpenetrated by said electrically conductive hydrogel adhesive layer, and adapted to be in contact with a patient's skin to maintain said medical electrode thereat, thus forming an adhesive-skin interface;
   an adhesive remover solvent;
   at least one compartment filled with said adhesive remover solvent and embedded via radiation in the intermixture of said adhesive layer and the filaments of the mesh grid, said at least one compartment being adapted for positioning in close proximity to the patient's skin when said medical electrode is attached to the patient's skin, wherein said at least one compartment is defined by an impermeable envelope substantially fully surrounding said adhesive remover solvent, wherein said impermeable envelope has a portion exposed through said adhesive layer at a side thereof opposite to said adhesive skin interface; and
   wherein, upon application of a force towards said exposed portion of said impermeable envelope sufficient to break the envelope, said adhesive remover solvent passes directly to said adhesive-skin interface, thereby facilitating said medical electrode removal from the patient's skin.

2. The medical electrode unit of claim 1, further comprising at least one protecting member covering said exposed portion of said impermeable envelope, and displaceable therefrom prior to the removal of said medical electrode from the patient's skin.

3. The medical electrode unit of claim 2, wherein said medical electrode further includes a non-conductive structure located atop said adhesive layer in surrounding relationship with said at least one compartment and said at least one protecting member.

4. The medical electrode unit of claim 1, wherein said adhesive layer contains 6%-10 weight % of polyethylene oxide (PEO), 5%-8 weight % of sodium chloride, and 80%-90 weight % of water.

5. The medical electrode unit of claim 1, wherein said adhesive layer contains 10 weight % of PEO, 5 weight % of sodium chloride, and 85 weight % of water.

6. The medical electrode unit of claim 1, wherein said adhesive remover solvent includes isopropyl alcohol.

7. The medical electrode unit of claim 1, wherein said impermeable envelope defining said at least one compartment is in direct contact with the patient's skin when said medical electrode is attached to the patient's skin.

8. The medical electrode unit of claim 1, wherein said at least one compartment has dimensions of approximately 1 cm in diameter and ½ cm in height.

9. The medical electrode unit of claim 1, wherein said at least one compartment contains about 1 ml of said adhesive remover solvent.

10. The medical electrode unit of claim 1, further comprising a wire connector electrically coupled to said electrically conductive hydrogel.

11. The medical electrode unit of claim 10, wherein said wire connector conducts biomedical electrical of interest to and from said elective hydrogel.

12. The medical electrode unit of claim 1, further comprising a medication added into said at least one compartment.

13. The medical electrode unit of claim 1, further comprising a medication added to said adhesive layer.

14. The medical electrode unit of claim 1, wherein said impermeable envelope is a plastic bubble.

15. A method of attaching a medical electrode unit to a patient's skin and subsequently removing said medical electrode unit therefrom, comprising the steps of:

forming a medical electrode including:
an electrically conductive hydrogel adhesive layer,
a non-conductive mesh grid formed with filaments and positioned underneath said adhesive layer, and interpenetrated by said electrically conductive hydrogel adhesive layer, and adapted to be in contact with a patient's skin to maintain said medical electrode unit thereat, thus forming an adhesive skin interface,
a predetermined amount of adhesive remover solvent,
at least one impermeable envelope embedded via radiation in the intermixture of said adhesive layer and the filaments of said mesh grid, said impermeable envelope substantially completely surrounding said adhesive remover solvent therein, wherein said impermeable envelope has a portion exposed through said electrically conductive adhesive layer at a site thereof opposite to said adhesive-skin interface, and
at least one protecting member removably covering said exposed portion of said at least one impermeable envelope;
attaching said medical electrode to the patient's skin with said adhesive layer in direct communication with the patient's skin; and
removing said medical electrode from the patient's skin by performing the steps of:
displacing said at least one protecting member from said exposed portion of said at least one impermeable envelope, and
applying a force to said exposed portion of said at least one impermeable envelope sufficient to break the same, thereby releasing said adhesive remover solvent directly to said adhesive layer at the adhesive-skin interface for neutralizing said adhesive.

16. The method of claim 15, wherein said at least one impermeable envelope is broken by application of a compressive force thereto.

* * * * *